(12) United States Patent
Minamino et al.

(10) Patent No.: US 10,519,093 B2
(45) Date of Patent: Dec. 31, 2019

(54) METHOD OF PRODUCING HYDROXYCINNAMIC ACIDS

(71) Applicant: Toray Industries, Inc., Tokyo (JP)

(72) Inventors: Atsushi Minamino, Kamakura (JP); Shigeyuki Funada, Kamakura (JP); Hiroyuki Kurihara, Kamakura (JP); Yuka Asahi, Kamakura (JP); Takuya Kasahara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/090,132

(22) PCT Filed: Mar. 28, 2017

(86) PCT No.: PCT/JP2017/012636
§ 371 (c)(1),
(2) Date: Sep. 28, 2018

(87) PCT Pub. No.: WO2017/170549
PCT Pub. Date: Oct. 5, 2017

(65) Prior Publication Data
US 2019/0112254 A1 Apr. 18, 2019

(30) Foreign Application Priority Data

Mar. 29, 2016 (JP) .................. 2016-066898

(51) Int. Cl.
| | | |
|---|---|---|
| C07C 45/00 | (2006.01) | |
| C07C 51/00 | (2006.01) | |
| C07C 59/00 | (2006.01) | |
| C07C 51/47 | (2006.01) | |
| C07C 45/79 | (2006.01) | |
| C07C 47/58 | (2006.01) | |
| C07C 59/52 | (2006.01) | |
| C07C 59/64 | (2006.01) | |
| C07C 51/43 | (2006.01) | |
| C07C 65/03 | (2006.01) | |

(52) U.S. Cl.
CPC .............. *C07C 51/47* (2013.01); *C07C 45/79* (2013.01); *C07C 47/58* (2013.01); *C07C 51/43* (2013.01); *C07C 59/52* (2013.01); *C07C 59/64* (2013.01); *C07C 65/03* (2013.01)

(58) Field of Classification Search
CPC ......... C07C 51/43; C07C 51/47; C07C 45/79; C07C 59/52; C07C 59/64
See application file for complete search history.

(56) References Cited

U.S. PATENT DOCUMENTS

2016/0145183 A1  5/2016  Revelant et al.

FOREIGN PATENT DOCUMENTS

| CN | 101559192 B | 4/2012 |
|---|---|---|
| JP | S59-192094 A | 10/1984 |
| JP | 2011-135861 A | 7/2011 |
| JP | 2011-140443 A | 7/2011 |
| JP | 2013-220067 A | 10/2013 |
| JP | 2014-023484 A | 2/2014 |
| WO | 2014/187784 A1 | 11/2014 |
| WO | 2016/005998 A1 | 1/2016 |

OTHER PUBLICATIONS

Tilay, A. et al., "Preparation of ferulic acid from agricultural wastes: its improved extraction and purification," *Journal of Agricultural and Food Chemistry*, Sep. 10, 2008, vol. 56, No. 17, pp. 7644-7648.

Salleh, N.H.M. et al., "Optimization of alkaline hydrolysis of paddy straw for ferulic acid extraction," *Industrial Crops and Products*, Nov. 2011, vol. 34, No. 3, pp. 1635-1640.

Xie, W. et al., "Optimization of Alkaline Hydrolysis of Lotus Root for Bound Ferulic Acid by Response Surface Methodology," *Food Science*, 2014, vol. 35, No. 10, pp. 18-22 [English summary provided].

*Primary Examiner* — Sikarl A Witherspoon
(74) *Attorney, Agent, or Firm* — DLA Piper LLP (US)

(57) ABSTRACT

A method efficiently produces hydroxycinnamic acids having a high quality, from a cellulose-containing biomass. More specifically, the method includes the steps of: obtaining an alkaline filtrate by allowing an alkaline aqueous medium to pass through a cellulose-containing biomass; obtaining a hydroxycinnamic acid extraction liquid by allowing the alkaline filtrate to repeatedly pass through the cellulose-containing biomass; and separating the hydroxycinnamic acid from the hydroxycinnamic acid extraction liquid.

16 Claims, No Drawings

METHOD OF PRODUCING HYDROXYCINNAMIC ACIDS

TECHNICAL FIELD

The present invention relates to a method of producing hydroxycinnamic acids from a cellulose-containing biomass.

BACKGROUND

Production processes of producing chemicals using saccharides as raw materials are employed in the production of various types of industrial raw materials. Currently, saccharides derived from edible raw materials such as sugarcane, starches and sugar beets are industrially used as raw material saccharides. However, in view of an increase in the cost of edible raw materials due to an increase in the world population in the future, or from an ethical point of view that the industrial use of edible raw materials may compete with the use thereof as food, it is a future challenge to develop processes to efficiently produce industrial raw materials from renewable, non-edible resources, namely, cellulose-containing biomasses.

Saccharides contained in cellulose-containing biomass raw materials are embedded within cell walls having a complicated structure. Accordingly, a technique of subjecting a biomass raw material to an alkaline treatment is known to efficiently obtain substances capable of being used as industrial raw materials, directly or indirectly.

For example, to improve the rate of enzymatic hydrolysis of cellulose, a technique is disclosed in which: a cellulose-containing product is subjected to an alkaline treatment by being brought into contact with an aqueous alkaline solution; the treated cellulose-containing product is washed with water and/or an aqueous acidic solution; and then an enzyme treatment is carried out by bringing the cellulose-containing product into contact with an aqueous solution containing a cellulolytic enzyme and a pH buffer, within the range of buffer solution concentration of from 0 to 250 mM (JP 2011-135861 A).

Further, a pretreatment method of carrying out an enzyme treatment of a biomass is disclosed, which method is characterized in that the biomass is supplied into a twin screw extruder; an aqueous solution of an alkaline compound is injected into the extruder while supplying the biomass; kneading the biomass and the aqueous solution in the extruder to allow a reaction to proceed (JP 59-192094 A).

To reduce the cost of producing sugars from a biomass, a method is disclosed in which; an herbaceous biomass or woody biomass is subjected to an alkaline treatment using an alkaline solution; solid-liquid separation is carried out to separate the resulting alkaline treated solution into an alkaline solution and a solid component; the separated alkaline solution is supplemented with an alkaline substance, to be recycled to the alkaline treatment step (JP 2014-23484 A).

Further, to improve the efficiency of enzymatic saccharification and drastically reduce the amount of neutralization effluent, an enzymatic saccharification method of a cellulose-based biomass raw material is disclosed, which method is characterized in that: a slurry containing a cellulose-based biomass raw material which has been cut, crushed, ground, mashed or powdered, calcium hydroxide, and water is prepared to carry out an alkaline treatment of the raw material, followed by solid-liquid separation; solids obtained by the solid-liquid separation, or a mixture of the solids and water is neutralized using carbon dioxide to be adjusted to a pH within the range of from 5 to 8; and an enzymatic saccharification reaction is carried out.

It is also disclosed that hydroxycinnamic acids including ferulic acid and coumaric acid can be obtained from the liquid component obtained by the above-described solid-liquid separation (JP 2013-220067 A).

Hydroxycinnamic acids contain a phenol group and a carboxyl group, and they can be converted into compounds having a styrene skeleton by decarbonation. Hydroxycinnamic acids have been reported to have various pharmacological functions, and it is expected that the application development thereof will be promoted in a variety of fields, leading to the activation of the market and the creation of novel industries. However, a method of efficiently obtaining hydroxycinnamic acids having a high quality from a cellulose-containing biomass is still needed.

It could therefore be helpful to provide a method of efficiently producing hydroxycinnamic acids from a cellulose-containing biomass and a method of producing hydroxycinnamic acids having a high quality from a cellulose-containing biomass.

SUMMARY

We found that it is possible to efficiently extract hydroxycinnamic acids by subjecting a cellulose-containing biomass to a specific treatment in which an alkaline filtrate is repeatedly used. Further, we found that the above-described treatment obtains the hydroxycinnamic acids at a markedly high purity.

We thus provide the following [1] to [15]:

[1] A method of producing hydroxycinnamic acids, the method including the steps of:

obtaining an alkaline filtrate by allowing an alkaline aqueous medium to pass through a cellulose-containing biomass; and obtaining a hydroxycinnamic acid extraction liquid by allowing the alkaline filtrate to repeatedly pass through the cellulose-containing biomass.

[2] The method of producing hydroxycinnamic acids according to [1], further including the step of separating the hydroxycinnamic acids from the hydroxycinnamic acid extraction liquid, by at least one method selected from an evaporative concentration method and a recrystallization method.

[3] The method of producing hydroxycinnamic acids according to [2], wherein the evaporative concentration method is carried out using a plate-type concentrator.

[4] The method of producing hydroxycinnamic acids according to any one of [1] to [3], wherein the hydroxycinnamic acids are hydroxycinnamic acid, hydroxybenzoic acid or methoxy group-substituted products of these compounds.

[5] The method of producing hydroxycinnamic acids according to any one of [1] to [4], wherein the hydroxycinnamic acids are at least one of coumaric acid, ferulic acid and vanillin [6] The method of producing hydroxycinnamic acids according to any one of [1] to [5], wherein the step of obtaining the alkaline filtrate includes supplying the cellulose-containing biomass and the alkaline aqueous medium to a filtration apparatus, and allowing the alkaline aqueous medium to pass through the cellulose-containing biomass using the filtration apparatus.

[7] The method of producing hydroxycinnamic acids according to any one of [1] to [6], wherein the alkaline aqueous medium or the alkaline filtrate is allowed to pass through the cellulose-containing biomass by self-weight filtration in the direction of gravity.

[8] The method of producing hydroxycinnamic acids according to any one of [1] to [7], wherein the alkaline aqueous medium and the alkaline filtrate are maintained substantially at the same temperature.
[9] The method of producing hydroxycinnamic acids according to any one of [1] to [8], wherein at least one of the alkaline aqueous medium and the alkaline filtrate has a temperature of 80° C. or higher and 100° C. or lower.
[10] The method of producing hydroxycinnamic acids according to any one of [1] to [9], wherein the alkaline filtrate includes acetic acid or a salt thereof.
[11] The method of producing hydroxycinnamic acids according to any one of [1] to [10], wherein the cellulose-containing biomass is one which has been sifted through a sieve with an aperture of 30 mm or more.
[12] The method of producing hydroxycinnamic acids according to any one of [1] to [11], wherein the cellulose-containing biomass is one which has been subjected to a dry grinding treatment.
[13] The method of producing a hydroxycinnamic acids according to according to any one of [1] to [12], wherein the cellulose-containing biomass is an herbaceous biomass.
[14] The method of producing hydroxycinnamic acids according to any one of [1] to [13], wherein the alkaline aqueous medium and the alkaline filtrate include at least one hydroxide selected from sodium hydroxide and potassium hydroxide.
[15] The method of producing hydroxycinnamic acids according to any one of [1] to [14], wherein the period of time during which the alkaline filtrate is repeatedly passed through the cellulose-containing biomass is 30 minutes or more and three hours or less.
[16] The method of producing hydroxycinnamic acids according to any one of [1] to [15], wherein the alkaline filtrate has a pH of 10 or more and 12 or less.

It is possible to efficiently obtain hydroxycinnamic acids from a cellulose-containing biomass, by repeatedly using the resulting alkaline filtrate. Our methods are advantageous in that they drastically reduce the amount of alkaline substance used and the reaction time in the production of hydroxycinnamic acids. Further, the methods are advantageous in that they produce hydroxycinnamic acids with a markedly high purity from a cellulose-containing biomass. Our method can be advantageously used in various types of applications such as industrial raw materials, livestock feed and food, and substitutes for antibiotics since the invention allows for efficiently producing hydroxycinnamic acids with a markedly high-purity.

DETAILED DESCRIPTION

The method of producing hydroxycinnamic acids is characterized in that it includes the steps of: obtaining an alkaline filtrate by allowing an alkaline aqueous medium to pass through a cellulose-containing biomass; obtaining a hydroxycinnamic acid extraction liquid by allowing the alkaline filtrate to repeatedly pass through the cellulose-containing biomass; and separating the hydroxycinnamic acids from the hydroxycinnamic acid extraction liquid. It is an unexpected fact that it is possible to efficiently obtain hydroxycinnamic acids with a markedly high purity by allowing the alkaline filtrate, as it is, to repeatedly pass through the cellulose-containing biomass.

The "hydroxycinnamic acids" refer to derivatives or analogs of cinnamic acid (3-phenyl-2-propenoic acid containing at least a hydroxy group. Specific examples of the hydroxycinnamic carboxylic acids include hydroxycinnamic acid, hydroxybenzoic acid and methoxy group-substituted products of these compounds; and preferred examples thereof include coumaric acid, ferulic acid, and vanillin.

It is preferred to first supply the cellulose-containing biomass and the alkaline aqueous medium into a filtration apparatus. The cellulose-containing biomass and the alkaline aqueous medium may be mixed in advance and then supplied into the filtration apparatus, or alternatively, the cellulose-containing biomass and the alkaline aqueous medium may be separately supplied into the filtration apparatus. However, it is preferred that the cellulose-containing biomass be supplied into the filtration apparatus in advance, and then the alkaline aqueous medium be supplied on top of the cellulose-containing biomass.

The cellulose-containing biomass refers to a biological resource containing at least cellulose. Suitable examples of the cellulose-containing biomass include herbaceous biomasses such as bagasse, switchgrass, napier grass, Erianthus, corn stover, straw (rice straw and wheat straw), and oil palm empty fruit bunches; woody biomasses such as wood, wood chips, and waste construction materials; and water environment-derived biomasses such as algae and seaweeds; and grain hull biomasses such as corn hulls, wheat hulls, soybean hulls, and rice hulls. However, herbaceous biomasses such as bagasse, rice straw and oil palm empty fruit bunches are more preferably used.

The shape of the cellulose-containing biomass is not particularly limited. However, the cellulose-containing biomass which has been subjected to a grinding treatment is preferred. The means for grinding is not particularly limited, and the grinding treatment can be carried out using a machine commonly used for the coarse grinding of various types of materials, such as, for example, a ball mill, a vibration mill, a cutter mill, a hammer mill, a Wiley mill, or a jet mill. The mechanical grinding as described above may be either a dry grinding or a wet grinding, but a dry grinding is preferred. The biomass may be classified as necessary, after being subjected to the grinding treatment. A preferred range of the grain size of the ground biomass can be selected depending on the aperture size of a sieve through which the cellulose-containing biomass is passed. A preferred range of the aperture size of the sieve through which the cellulose-containing biomass is passed may be, for example, about 8 mm or more, about 8 mm or more and about 20 mm or less, about 20 mm or more, about 20 mm or more and about 30 mm or less, about 30 mm or more, about 30 mm or more and about 50 mm or less, about 50 mm or more, about 50 mm or more and about 70 mm or less, or about 70 mm or more.

Further, the cellulose-containing biomass preferably has a moisture content of, for example, about 3% or more, about 3% or more and about 60% or less, about 5% or more, about 5% or more and about 60% or less, about 5% or more and about 55% or less, or about 5% or more and about 55% or less, but not particularly limited thereto.

The alkaline aqueous medium may be, for example, an alkaline aqueous solution such as an aqueous medium containing ammonia, ammonia water, or a hydroxide. However, the alkaline aqueous medium is preferably an aqueous medium containing at least one hydroxide selected from sodium hydroxide and potassium hydroxide, and more preferably an aqueous solution of sodium hydroxide or an aqueous solution of potassium hydroxide.

The upper limit value of the alkali concentration of the alkaline aqueous medium is preferably about 3, 2, 1.5, 1.0, 0.7, 0.6, 0.5, 0.4 or 0.3% by weight; and the lower limit value thereof is preferably about 0, 0.5, 0.1, 0.2, 0.3, 0.4 or 0.5% by weight, but not particularly limited thereto. The alkaline aqueous medium preferably has an alkali concentration of, for example, about 0.05% by weight or more and about 0.3% by weight or less, about 0.1% by weight or more and about 3% by weight or less, or about 0.1% by weight or more and about 2% by weight or less; more preferably of about from 0.1 to 2% by weight, about 0.3% by weight or more and about 1.5% by weight or less, or about 0.7% by weight or more and about 1.5% by weight or less; and still more preferably about 0.3% by weight or more and about 1.5% by weight or less, or about 0.7% by weight or more and about 1.5% by weight or less.

Further, the lower limit value of the pH of the alkaline aqueous medium is not particularly limited, as long as the pH is within an alkaline range. However, the alkaline aqueous medium has a pH of 7 or more, preferably a pH of 8 or more, more preferably a pH of 9 or more, and still more preferably a pH of 10 or more. The upper limit value of the pH of the alkaline aqueous medium is not particularly limited, as long as the pH is less than 14, and it can be set to a pH of 12 or less, from the viewpoint of reducing the amount of alkaline substance used. The alkaline aqueous medium preferably has a pH of, for example, 7 or more and 13.5 or less, or 8 or more and 13.5 or less, more preferably has a pH of 9 or more and 13.5 or less, and still more preferably has a pH of 10 or more and 12 or less.

Acetic acid or a salt thereof may be optionally added to the alkaline aqueous medium. The addition of acetic acid or a salt thereof to the alkaline aqueous medium is preferred in that it improves the reaction efficiency. A preferred concentration of acetic acid in the alkaline aqueous medium is, for example, about 0.05% by weight or more and about 5.0% by weight or less, about 0.08% by weight or more and about 3.0% by weight or less, about 0.08% by weight or more and about 2.5% by weight or less, about 0.08% by weight or more and about 2.3% by weight or less, or about 0.1% by weight or more and about 2.0% by weight or less; and more preferably about 0.08% by weight or more and about 2.3% by weight or less, or about 0.1% by weight or more and about 2.0% by weight or less.

The upper limit value of the temperature of the alkaline aqueous medium is preferably about 110, 100, 95, 90, 80, 75 or 70° C., and the lower limit value thereof is preferably about 35, 40, 50, 60 or 65° C., but not particularly limited thereto. The alkaline aqueous medium preferably has a temperature of, for example, about 35° C. or more and about 100° C. or less, about 40° C. or more and about 100° C. or less, about 50° C. or more and about 100° C. or less, about 60° C. or more and about 100° C. or less, about 65° C. or more and about 100° C. or less, or about 80° C. or more and about 100° C. or less; more preferably has a temperature of about 60° C. or more and about 100° C. or less, about 65° C. or more and about 100° C. or less, or about 80° C. or more and about 100° C. or less; and still more preferably has a temperature of about 65° C. or more and about 100° C. or less, or about 80° C. or more and about 100° C. or less.

The weight ratio of the alkaline aqueous medium to the cellulose-containing biomass (in dry weight) is preferably, for example, 100:1 to 2:1, 90:1 to 3:1, 50:1 to 5:1, 30:1 to 5:1, 25:1 to 7:1, 25:1 to 7:1, 25:1 to 5:1, or 20:1 to 5:1, but not particularly limited thereto.

Further, it is also possible to select the ratio of the alkaline aqueous medium to the cellulose-containing biomass (in dry weight), using as an index the amount of alkaline substance used (also referred to as an alkaline reaction amount) to be described later in Reference Example 5. A preferred range of the amount of alkaline substance used is, for example, about 20 mg/g or more and about 300 mg/g or less, about 30 mg/g or more and about 200 mg/g or less, about 40 mg/g or more and about 200 mg/g or less, about 45 mg/g or more and about 180 mg/g or less, about 45 mg/g or more and about 150 mg/g or less, about 45 mg/g or more and about 120 mg/g or less, about 50 mg/g or more and about 100 mg/g or less, or about 50 mg/g or more and about 90 mg/g or less; and a more preferred range of the amount of alkaline substance used is about 45 mg/g or more and about 120 mg/g or less, about 50 mg/g or more and about 100 mg/g or less, or about 50 mg/g or more and about 90 mg/g or less.

The filtration apparatus is not particularly limited, as long as it carries out our method. However, it is preferred that the filtration apparatus at least includes: a biomass accommodating portion to accommodate at least the cellulose-containing biomass; a filtering portion allowing the alkaline aqueous medium to pass through the cellulose-containing biomass; and a filtrate circulating portion that collects and circulates the alkaline filtrate obtained from the filtering portion.

The shape of the biomass accommodating portion of the filtration apparatus is not particularly limited, and the biomass accommodating portion may be in the shape of a cylinder, a box, a membrane, slits, a plate, a belt (movable type) or the like. It is preferred that the biomass accommodating portion have at least one opening to supply the cellulose-containing biomass, the alkaline aqueous medium and the alkaline filtrate into the biomass accommodating portion, at an upper surface or a side surface thereof, and be disposed adjacent to the filtering portion. Further, the filtering portion is preferably disposed at a bottom surface of the biomass accommodating portion. In addition, the filtration apparatus preferably has a structure in which the biomass accommodating portion and the filtering portion are integrally formed.

The size of the biomass accommodating portion is not particularly limited, and the biomass accommodating portion preferably has a capacity or an area that accommodates at least the cellulose-containing biomass. For example, when the biomass accommodating portion is in the form of a cylinder or a box, the biomass accommodating portion preferably has a capacity containing both the cellulose-containing biomass and the alkaline aqueous medium. When the biomass accommodating portion is in the form of a plate or a belt, the biomass accommodating portion preferably has a sufficient area so that the cellulose-containing biomass can be disposed on the biomass accommodating portion.

The shape of the filtering portion is not particularly limited, but the filtering portion is preferably in the shape of a plate, a membrane or a belt since the cellulose-containing biomass is disposed thereon to carry out the filtration. Further, the filtering portion preferably has pores that allow the alkaline aqueous medium to pass therethrough, without allowing the cellulose-containing biomass to pass therethrough. The filtering portion can be composed of a microfiltration membrane (MF) or an ultrafiltration membrane (UF).

The average pore diameter of the pores of the filtering portion can be selected as appropriate depending on the grain size of the cellulose-containing biomass. The filtering portion preferably has an average pore diameter of, for example, 0.001 μm to 5 mm, 0.01 μm to 5 mm, or 0.1 μm to 5 mm. The "average pore diameter" as used herein refers to a mean flow pore diameter, as measured by the mean flow-point method, using a porometer (manufactured by Coster Corporation).

The shape of the pores of the filtering portion is not particularly limited, and the pores may be, for example, in the shape of cuts extending in one direction, such as slits. The filtering portion preferably has an aperture ratio of 5% or more and 60% or less, and more preferably 10% or more and 40% or less, but not particularly limited thereto. Adjusting the aperture ratio within the above-described range is advantageous in that it prevents fine particles of the biomass from clogging to the filtering portion to result in a reduced filtration speed or a failure to hold the biomass on the filtration apparatus. When the filtering portion has pores in the shape of cuts such as slits, the width thereof is preferably 0.001 µm to 5 mm, 0.01 µm to 5 mm, or 0.1 µm to 5 mm, which is the same as the range described above for the average pore diameter.

Materials for the filtering portion are not particularly limited, and examples thereof include: organic materials such as polysulfone, polyethersulfone, chlorinated polyethylene, polypropylene, polyolefin, polyvinyl alcohol, polymethyl methacrylate, polyvinylidene fluoride, polytetrafluorinated ethylene, and polyacrylate; metals such as iron, titanium, aluminum, and stainless steel, and inorganic materials such as ceramics.

The shape of the filtrate circulating portion is not particularly limited, as long as it collects the alkaline filtrate obtained from the filtering portion to be reused for the filtration. A suitable filtrate circulating portion at least includes a collecting container portion (a bucket or the like) such as, for example, one disposed under the filtering portion and has an opening to collect the filtrate.

The filtrate circulating portion may be provided fixed to the filtration apparatus, or disposed to be transportable or movable. Particularly, when the filtrate circulating portion is transportable or movable, the filtrate circulating portion can be transported to the vicinity of the biomass accommodating portion after collecting the alkaline filtrate, for example, and the collected alkaline filtrate can be poured into the biomass accommodating portion, as it is, to carry out recirculation filtration.

When the filtrate circulating portion is not usually transported or moved, the filtrate circulating portion may further include a line portion (a pipe or the like) that circulates the alkaline filtrate from the filtrate circulating portion to the biomass accommodating portion.

The line portion preferably includes an injection inlet (such as an opening in the form of a shower nozzle) to reinject the alkaline filtrate into the biomass accommodating portion. Further, it is preferred that the filtrate circulating portion further include a pump that provides a driving force to circulate the alkaline filtrate. In addition, the filtrate circulating portion preferably has a function that maintains the temperature of, or heating, the filtrate. It is advantageous to use a filtrate circulating portion having such a function of maintaining the temperature of, or heating, the filtrate, since it prevents the reaction from being disturbed due to a temperature drop, particularly when the initial reaction temperature is high. It is more preferred that the filtrate circulating portion of the filtration apparatus be capable of forcibly maintaining or increasing the temperature of the filtrate, by internally sharing vapor or hot water, entirely or partially within the filtrate circulating portion, by a jacket system or a trace system.

Materials for the filtrate circulating portion and the biomass accommodating portion are not particularly limited, and the same materials as those described above for the filtering portion can be used, for example.

It possible to use a known circulation-type extraction (filtration) apparatus as the filtration apparatus.

Suitable examples of the filtration apparatus include a belt type filtration apparatus (LM, manufactured by Desmet Ballestra), a basket type filtration apparatus, a rotary type filtration apparatus (Carousel, Rotocell, REFLEX), a Bonot type filtration apparatus, and a screen-filtration type filtration apparatus. More preferred is an in-tank screen filtration apparatus (manufactured by Izumi Food Machinery Co., Ltd.), or a belt conveyor-type screen filtration apparatus (Model 2 or Model 3; manufactured by Crown Iron Works Company). The use of such a circulation-type extraction (filtration) apparatus is advantageous since it reduces the cost of industrial equipment compared to the use of a conventional pretreatment apparatus using a high-temperature or a high-pressure container.

It is possible to use a plurality of filtration apparatuses connected in parallel. In such an example, the respective filtration apparatuses can be connected, for example, such that: a first alkaline filtrate discharged from a first filtration apparatus is injected into a second filtration apparatus through a first line portion; a second alkaline filtrate discharged from the second filtration apparatus is injected into a third filtration apparatus through a second line portion; and a third alkaline filtrate discharged from the third filtration apparatus is injected into the first filtration apparatus through a third line portion.

The filtration apparatus may include one biomass accommodating portion, one filtering portion, and a plurality of filtrate circulating portions. In such an example, for example, the biomass accommodating portion and the filtering portion can be formed integrally, and can be formed in the shape of a movable belt having pores. Further, the plurality of filtrate circulating portions can be provided under the movable belt. It is possible to carry out a pretreatment reaction by circulating the alkaline filtrate while moving the biomass by the belt, and thus, it is advantageous from the viewpoint of improving reaction efficiency.

Further, in another preferred example, a filtration apparatus may be used that is capable of bringing the cellulose-containing biomass into facing contact with the alkaline aqueous medium or the alkaline filtrate. Such a filtration apparatus may be provided with, for example, lids that can be opened and closed to the opening and to the contact surface with the filtering portion so that the biomass accommodating portion can be sealed during the facing contact. Further, the filtration apparatus may further be provided with a pressurizing portion to apply a pressure required during the facing contact. The use of such a filtration apparatus capable of allowing such facing contact is advantageous from the viewpoint of further improving reaction efficiency.

An alkaline aqueous medium is allowed to pass through a cellulose-containing biomass to obtain an alkaline filtrate. The alkaline aqueous medium is preferably allowed to pass through the cellulose-containing biomass by self-weight filtration in the direction of gravity, which utilizes the weight of the alkaline solution. The above-described self-weight filtration is advantageous, since it achieves a moderate passing rate to improve reaction efficiency, and serves to compact the biomass to realize a uniform reaction. When the liquid is forced to pass through the cellulose-containing biomass using a pump, in particular, the self-weight filtration is especially preferred from the viewpoint of realizing an effective and uniform reaction.

Further, the alkaline filtrate may have a pH within the same range as that of the alkaline aqueous medium, and the alkaline filtrate preferably has a pH of, for example, 7 or more and 12 or less, or 8 or more and 12 or less, more preferably 9 or more and 12 or less, and still more preferably of 10 or more and 12 or less. The pH of the alkaline filtrate tends to decrease as the reaction proceeds. This is because soluble lignin components function as neutralizers as the alkaline reaction proceeds and, thus, it is possible to measure how far the reaction has proceeded, based on the degree of pH decrease. In particular, the pH range of the alkaline filtrate at the completion of the recirculation filtration (after the reaction) can be adjusted as appropriate by controlling the initial alkali concentration and the like. However, the pH is preferably, for example, 7 or more and 12.5 or less, or 8 or more and 12.5 or less, more preferably 9 or more and 12 or less, and still more preferably 10 or more and 12 or less. Measuring and determining whether the pH of the alkaline filtrate is within the above-described range or not, is an effective means to evaluate if the reaction has proceeded to a level sufficient for carrying out a subsequent hydrolysis step. Further, the alkaline filtrate is preferably used as it is in the recirculation filtration without further adding an alkaline substance thereto. It is possible to improve the reaction efficiency without further adding an alkaline substance to the alkaline filtrate, and thus it is advantageous in reducing the cost.

Further, it is preferred that the alkaline filtrate substantially maintain the temperature of the alkaline aqueous medium before being filtered. For example, a suitable temperature of the alkaline filtrate may be substantially within the same range as that of the alkaline aqueous medium (within the range of about ±0.5 to 1° C.). The alkaline filtrate preferably has a temperature of, for example, about 35° C. or more and about 100° C. or less, about 40° C. or more and about 100° C. or less, about 50° C. or more and about 100° C. or less, about 60° C. or more and about 100° C. or less, about 65° C. or more and about 100° C. or less, or about 80° C. or more and about 100° C. or less; more preferably has a temperature of about 60° C. or more and about 100° C. or less, about 65° C. or more and about 100° C. or less, or about 80° C. or more and about 100° C. or less; and still more preferably has a temperature of about 65° C. or more and about 100° C. or less, or about 80° C. or more and about 100° C. or less. The temperature of the alkaline filtrate can be maintained within the above range by installing a known temperature maintenance device or a heating device to the filtration apparatus.

Further, the alkaline filtrate obtained by allowing the alkaline aqueous medium to pass through the cellulose-containing biomass is allowed to repeatedly pass through the cellulose-containing biomass as described above to prepare a hydroxycinnamic acid extraction liquid. A circulation step in which the alkaline filtrate is repeatedly passed through the cellulose-containing biomass can be carried out using the filtration apparatus described above.

A suitable period of time during which the alkaline filtrate is repeatedly passed through the cellulose-containing biomass is, for example, about 20 minutes or more and about 72 hours or less, about 20 minutes or more and about 48 hours or less, about 20 minutes or more and about 24 hours or less, about 30 minutes or more and about 48 hours or less, about 30 minutes or more and about 24 hours or less, about 30 minutes or more and about 12 hours or less, about 30 minutes or more and about 6 hours or less, or about 30 minutes or more and about 3 hours or less, but not particularly limited thereto.

A suitable number of times for which the alkaline filtrate is repeatedly passed through the cellulose-containing biomass is, for example, at least twice or more, twice or more and 20,000 times or less, twice or more and 10,000 times or less, twice or more and 1,000 times or less, three or more and 10,000 times or less, three times or more and 1,000 times or less, or three times or more and 100 times or less, but not particularly limited thereto.

By carrying out the above-described recirculation filtration, a hydroxycinnamic acid extraction liquid and a cellulose-containing solid component can be obtained from the cellulose-containing biomass. The cellulose-containing solid component obtained by the filtration may further be subjected to filtration, pressurization and the like, using a known apparatus, and the resulting liquid component may be added to the hydroxycinnamic acid extraction liquid.

It is possible to efficiently extract hydroxycinnamic acids including coumaric acid, ferulic acid and vanillin into the hydroxycinnamic acid extraction liquid. Such hydroxycinnamic acids can be advantageously used as novel biodegradable polymer raw materials and the like, and it is advantageous from the viewpoint of industrial production. The concentration of each of coumaric acid, ferulic acid, and vanillin in the hydroxycinnamic acid extraction liquid can be selected as appropriate depending on the reaction conditions and the like of the respective steps. A suitable concentration of the coumaric acid in the above-described extraction liquid is, for example, about 500 mg/L or more and about 2,000 mg/L or less, about 600 mg/L or more and about 2,000 mg/L or less, about 700 mg/L or more and about 2,000 g/L or less, about 750 mg/L or more and about 2,000 mg/L or less, about 750 g/L or more and about 1,500 mg/L or less, or about 750 mg/L or more and about 1,200 mg/L or less.

A suitable concentration of ferulic acid in the above-described extraction liquid is, for example, about 30 mg/L or more and about 500 mg/L or less, about 40 mg/L or more and about 400 mg/L or less, about 50 mg/L or more and about 300 mg/L or less, about 50 mg/L or more and about 250 mg/L or less, about 60 mg/L or more and about 250 mg/L or less, or about 60 mg/L or more and about 250 mg/L or less.

A suitable concentration of vanillin in the above-described extraction liquid is, for example, about 2 mg/L or more and about 30 mg/L or less, about 3 mg/L or more and about 20 mg/L or less, about 4 mg/L or more and about 20 mg/L or less, about 5 mg/L or more and about 20 mg/L or less, or about 5 mg/L or more and about 15 mg/L or less.

It is possible to separate and extract hydroxycinnamic acids from the above-described extraction liquid. The separation method described above is not particularly limited, and examples thereof include known methods such as an evaporative concentration method, filtration, normal pressure drying, freeze drying, evaporation to dryness, and recrystallization. Among these, the evaporative concentration method is preferred. An apparatus to be used to carry out the evaporative concentration method is not particularly limited. However, a plate-type concentrator is preferred. It is advantageous to use a plate-type concentrator, since it allows for control of the generation of bubbles in the extraction liquid to prevent hydroxycinnamic acids from mixing into the distillate, and thus enables to efficiently obtain the hydroxycinnamic acids.

Further, the above-described extraction liquid can be advantageously used to produce crystals of high-purity hydroxycinnamic acids. For example, when the extraction liquid is optionally concentrated, and then left to stand under the conditions of about 4° C. at 24 hours, the purity of the hydroxycinnamic acids in the resulting crystals is at least 95% or more, more preferably 98% or more, and still more preferably 99% or more. Further, the crystals of the above-described hydroxycinnamic acids are preferably mixed crystals of coumaric acid and ferulic acid.

EXAMPLES

Our methods will now be described more specifically. However, this disclosure is in no way limited by the Examples. Units and measurement methods described in the present specification are in accordance with Japanese Industrial Standard (JIS), unless otherwise specified.

Reference Example 1: Method of Measuring Concentrations of Hydroxycinnamic Acids The concentrations of hydroxycinnamic acids (such as coumaric acid and ferulic acid) and other aromatic compounds (such as vanillin) contained in a liquid were analyzed by HPLC under the conditions shown below, and quantified based on comparison with standard samples.
Columns: Synergi HidroRP 4.6 mm×250 mm (manufactured by Phenomenex Inc.)
Mobile phase: acetonitrile—0.1% $H_3PO_4$ (flow velocity: 1.0 mL/min)
Detection method: UV (283 nm)
Temperature: 40° C.

Reference Example 2: Method of Measuring Concentrations of Organic Acids

The concentrations organic acids (acetic acid and formic acid) contained were analyzed by HPLC under the conditions shown below, and quantified based on comparison with standard samples.
Columns: Shim-Pack SPR-H and Shim-Pack SCR101H (manufactured by Shimadzu Corporation) connected in series
Mobile phase: 5 mM p-toluenesulfonic acid (flow velocity: 0.8 mL/min)
Reaction liquid: 5 mM p-toluenesulfonic acid, 20 mM BisTris, 0.1 mM EDTA.2Na (flow velocity: 0.8 mL/min)
Detection method: electric conductivity
Temperature: 45° C.

Reference Example 3: Method of Measuring Moisture Content

The moisture content of each of the cellulose-containing biomasses used in the Examples was measured. Using an infrared moisture meter ("FD-720", manufactured by Kett Electric Laboratory), a sample was maintained at a temperature of 120° C., and the moisture content of the sample was measured, which is a value obtained from the difference between the stable value after the evaporation and the initial value. The moisture content of each of the raw materials used in the Examples is shown in Table 1. Bagasse, rice straw and oil palm empty fruit bunches are classified as herbaceous biomass.

TABLE 1

| Raw material | Moisture content |
| --- | --- |
| Bagasse | 50% |
| Rice straw | 10% |
| Oil palm empty fruit bunches | 15% |
| Wood chips (cedar) | 5% |

Reference Example 4: Method of Calculating Alkaline Reaction Amount

When calculating the alkaline reaction amount in cases where b (g) of a y (%) aqueous solution of sodium hydroxide, for example, is added to a (g) of a cellulose-containing biomass raw material having a moisture content of x (%), for example, to allow a reaction to occur, the alkaline reaction amount (unit: mg/g-dry biomass) is represented by Equation (1):

$$\text{Alkaline reaction amount} = y \times b \times 1000/\{(100-x) \times a\} \quad (1)$$

Example 1: Effect of Using Filtration Method (Reduction in Reaction Time and Reduction in Amount of Alkaline Substance Used)

A cutter mill (Baryonyx BRX-400; manufactured by Nara Machinery Co., Ltd.) was used to grind bagasse. The aperture size of the sieve of the cutter mill was set to 50 mm, and the grinding was carried out at a rotational velocity of 600 rpm, while supplying bagasse at a supply rate of 1,000 kg/hr.

A quantity of 5.0 kg of the resulting ground bagasse (moisture content: 50%) was charged into a multifunctional extraction apparatus (manufactured by Izumi Food Machinery Co., Ltd.), and 45 kg of an aqueous solution of sodium hydroxide having a predetermined concentration (initial temperature: 90° C., pH: around 13) was added thereto, through a spray ball provided at the upper portion of the tank of the multifunctional extraction apparatus. A liquid (alkaline filtrate) obtained by self-weight filtration through a filtration net provided within the tank was repeatedly introduced into the multifunctional extraction apparatus through the spray ball. A heating mechanism was provided between the filtration net and the spray ball provided at the upper portion, and a reaction was carried out for a predetermined period of time, while monitoring the temperature. During the reaction, the temperature of the alkaline filtrate was controlled to be not lower than 90° C. An impeller equipped to the above-described multifunctional extraction apparatus was not used. The bagasse and the cellulose-containing solid component were placed on the filtration net, and an operation of shaping them with an impeller or the like, or an operation of forming them into a slurry was not carried out. The alkaline filtrate was repeatedly subjected to recirculation filtration during the predetermined reaction time, and separated into an extraction liquid and a cellulose-containing solid component by filtration.

Further, the solid component was filtered through a stainless steel strainer with an aperture of 3 mm, and the solid component remaining on the upper surface of the strainer was pressed with a hand against the strainer surface, to squeeze out the remaining liquid. The thus obtained liquid component was added to the extraction liquid. The resulting final extraction liquid obtained for each set of reaction conditions was analyzed with the method described in Reference Example 1, and the results are shown in Table 2. The results revealed that hydroxycinnamic acids have been efficiently obtained by self-weight filtration, as compared to Comparative Examples 1 and 2. Further, we found, from the results obtained at the alkali concentration of 0.5%, that the reaction status in the extraction liquid can be generally predicted based on the pH value.

TABLE 2

| Alkali concentration [%] | Initial pH | Alkaline reaction amount [mg/g-dry] | Alkaline reaction time [hr] | Coumaric acid [mg/L] | Ferulic acid [mg/L] | Vanillin [mg/L] | pH* |
|---|---|---|---|---|---|---|---|
| 0.3 | 13.0 | 54  | 2.0 | 950  | 170 | 7  | 11.0 |
| 0.4 | 13.1 | 72  | 2.0 | 990  | 178 | 8  | 10.8 |
| 0.5 | 13.2 | 90  | 2.0 | 1150 | 195 | 10 | 10.5 |
| 0.5 | 13.3 | 108 | 2.0 | 1200 | 200 | 11 | 10.2 |
| 0.5 | 13.2 | 90  | 0.5 | 930  | 175 | 8  | 11.4 |
| 0.5 | 13.2 | 90  | 1.0 | 1000 | 180 | 9  | 10.8 |
| 0.5 | 13.2 | 90  | 1.5 | 1100 | 190 | 10 | 10.6 |
| 0.5 | 13.2 | 90  | 3.0 | 1200 | 200 | 11 | 10.0 |

*pH at the completion of reaction

Comparative Example 1: When Reaction is Carried Out Under Stand-Still Conditions (Reaction Time and Amount of Alkaline Substance Used)

A quantity of 0.5 kg of ground bagasse (moisture content: 50%) obtained in Example 1 and 4.5 kg of an aqueous solution of sodium hydroxide having a predetermined concentration were introduced into a stainless steel container with a capacity of 10 L. The contents were heated with a gas stove while stirring, until the internal temperature reached 90° C. Subsequently, the stainless steel container containing the bagasse and the aqueous solution of sodium hydroxide was placed in a convection oven which is in a stable state at 90° C., and then left to stand to obtain a sample. At this time, the retention time was taken as the reaction time, and the concentration of sodium hydroxide was varied to prepare a plurality of samples of aqueous sodium hydroxide solutions, as shown in Table 3.

Each of the resulting samples was filtered through a stainless steel strainer with an aperture of 3 mm to obtain a filtrate, and the solid component remaining on the upper surface of the strainer was pressed with a hand against the strainer surface, to squeeze out the remaining liquid. The thus obtained liquid component was added to the filtrate, to obtain an extraction liquid. The resulting extraction liquid obtained for each set of reaction conditions was analyzed with the method described in Reference Example 1, and the results are shown in Table 3. The pH of each liquid component after the reaction is also shown below.

TABLE 3

| Alkali concentration [%] | Alkaline reaction amount [mg/g] | Alkaline reaction time [hr] | Coumaric acid [mg/L] | Ferulic acid [mg/L] | Vanillin [mg/L] | pH |
|---|---|---|---|---|---|---|
| 0.3 | 54  | 2.0 | 780 | 135 | 5 | 11.8 |
| 0.4 | 72  | 2.0 | 810 | 145 | 6 | 11.6 |
| 0.5 | 90  | 2.0 | 900 | 160 | 6 | 11.4 |
| 0.6 | 108 | 2.0 | 950 | 170 | 6 | 11.4 |
| 0.5 | 90  | 0.5 | 800 | 140 | 5 | 12.0 |
| 0.5 | 90  | 1.0 | 820 | 150 | 6 | 11.8 |
| 0.5 | 90  | 1.5 | 850 | 160 | 6 | 11.6 |
| 0.5 | 90  | 3.0 | 950 | 170 | 6 | 11.4 |

Comparative Example 2: When Reaction is Carried Out with Stirring (Reaction Time and Amount of Alkaline Substance Used)

A quantity of 0.5 kg of ground bagasse (moisture content: 50%) obtained in Example 1 and 4.5 kg of an aqueous solution of sodium hydroxide having a predetermined concentration were introduced into a reaction vessel with a capacity of 8 L. An electrothermal heater-type Jacket was attached to the reaction vessel, and the contents of the vessel were heated while stirring, until the internal temperature reached 90° C. The time point at which the internal temperature reached 90° C. was taken as the start of the reaction time, and a stirring reaction was carried out for a predetermined period of time to obtain a sample for each set of reaction conditions.

The resulting sample was filtered through a stainless steel strainer with an aperture of 3 mm to obtain a filtrate, and the solid component remaining on the upper surface of the strainer was pressed with a hand against the strainer surface, to squeeze out the remaining liquid. The thus obtained liquid component was added to the filtrate to obtain an extraction liquid. The resulting extraction liquid obtained for each set of reaction conditions was analyzed with the method described in Reference Example 1, and the results are shown in Table 4. The pH of each liquid component after the reaction is also shown below.

TABLE 4

| Alkali concentration [%] | Alkaline reaction amount [mg/g] | Alkaline reaction time [hr] | Coumaric acid [mg/L] | Ferulic acid [mg/L] | Vanillin [mg/L] |
|---|---|---|---|---|---|
| 0.3 | 54  | 2.0 | 800  | 140 | 5 |
| 0.4 | 72  | 2.0 | 840  | 155 | 6 |
| 0.5 | 90  | 2.0 | 920  | 170 | 7 |
| 0.6 | 108 | 2.0 | 1000 | 180 | 7 |
| 0.5 | 90  | 0.5 | 810  | 150 | 5 |
| 0.5 | 90  | 1.0 | 840  | 160 | 6 |
| 0.5 | 90  | 1.5 | 890  | 170 | 6 |
| 0.5 | 90  | 3.0 | 1000 | 180 | 7 |

Example 2: Effect Obtained when Acetic Acid is Added

The reaction conditions were unified to those described in Example 1 in which the concentration of the aqueous solution of sodium hydroxide was set to 0.5%, and the reaction time was set to 2.0 hours. In addition, acetic acid was added to the aqueous solution of sodium hydroxide to prepare samples having predetermined concentrations shown in Table 5, and an examination was carried out. Filtration was performed to obtain an extraction liquid and a cellulose-containing solid component, for each acetic acid concentration.

Further, the solid component was filtered through a stainless steel strainer with an aperture of 3 mm, in the same manner as in Example 1, and the solid component remaining on the upper surface of the strainer was pressed with a hand against the strainer surface to squeeze out the remaining liquid. The thus obtained liquid component was added to the extraction liquid. The resulting final extraction liquid obtained for each acetic acid concentration was analyzed with the method described in Reference Example 1, and the results are shown in Table 5. The results revealed that acetic acid in the reaction liquid has contributed to the reaction.

TABLE 5

| Acetic acid concentration [%] | Coumaric acid [mg/L] | Ferulic acid [mg/L] | Vanillin [mg/L] |
| --- | --- | --- | --- |
| Not added (Example 1) | 1150 | 195 | 10 |
| 0.1 | 1150 | 195 | 10 |
| 0.2 | 1180 | 200 | 10 |
| 0.5 | 1220 | 205 | 11 |
| 1.0 | 1250 | 210 | 12 |
| 2.0 | 1250 | 210 | 12 |

Example 3: Examination Regarding Grinding Degree of Bagasse

A cutter mill (Baryonyx BRX-400; manufactured by Nara Machinery Co., Ltd.) was used to grind bagasse, and an examination was carried out. The aperture size of the sieve of the cutter mill was set to 8 mm, 20 mm, 30 mm, 50 mm (Example 1), or 70 mm to carry out an examination, and an extraction liquid and a residue were obtained by filtration, for each aperture size. The reaction conditions were unified to those described in Example 1 in which the concentration of the aqueous solution of sodium hydroxide was set to 0.5% and the reaction time was set to 2.0 hours.

Further, the resulting cellulose-containing solid component was filtered through a stainless steel strainer with an aperture of 3 mm, in the same manner as in Example 1 and the solid component remaining on the upper surface of the strainer was pressed with a hand against the strainer surface to squeeze out the remaining liquid. The thus obtained liquid component was added to the extraction liquid. The resulting final extraction liquid obtained for each aperture size was analyzed with the method described in Reference Example 1, and the results are shown in Table 6.

TABLE 6

| Aperture size of sieve of grinder mm | Coumaric acid [mg/L] | Ferulic acid [mg/L] | Vanillin [mg/L] |
| --- | --- | --- | --- |
| 8 | 900 | 165 | 6 |
| 20 | 950 | 170 | 7 |
| 30 | 1150 | 195 | 10 |
| 50 (Example 1) | 1150 | 195 | 10 |
| 70 | 1150 | 195 | 10 |

Example 4: Examination of Other Raw Materials: Rice Straw, Oil Palm Empty Fruit Bunches and Wood Chips (Cedar)

Rice straw (moisture content: 10%), oil palm empty fruit bunches (moisture content: 15%), and Cedar wood chips (moisture content: 5%) were each ground using a cutter mill under the same conditions as in Example 1, to obtain respective raw material biomasses.

Subsequently, using the same multifunctional extraction apparatus as one used in Example 1, 52 kg of a 0.43% aqueous solution of sodium hydroxide was added to each of the raw material biomasses in amounts shown in Table 7 to achieve the alkaline reaction amount of about 90 mg/g-dry biomass, and an examination was carried out. Thereafter, the reaction was carried out in the same manner as in Example 1 under the conditions of 90° C. for two hours, and an extraction liquid and a cellulose-containing solid component were obtained by filtration, for each raw material biomass.

Further, the solid component was filtered through a stainless steel strainer with an aperture of 3 mm, in the same manner as in Example 1, and the solid component remaining on the upper surface of the strainer was pressed with a hand against the strainer surface to squeeze out the remaining liquid. The thus obtained liquid component was added to the extraction liquid. The resulting final extraction liquid obtained for each raw material biomass was analyzed with the method described in Reference Example 1, and the results are shown in Table 8.

TABLE 7

| Raw material Biomass Unit | Moisture content % | Charged amount kg | Added amount of alkaline solution kg | Alkali concentration % | Alkaline reaction amount mg/g |
| --- | --- | --- | --- | --- | --- |
| Rice straw | 10 | 2.75 | 52 | 0.43 | 90.3 |
| Oil palm empty fruit bunches | 15 | 2.9 | 52 | 0.43 | 901.7 |
| Wood chips (cedar) | 5 | 2.6 | 52 | 0.43 | 90.5 |

TABLE 8

| Raw material | Coumaric acid [mg/L] | Ferulic acid [mg/L] | Vanillin [mg/L] |
| --- | --- | --- | --- |
| Rice straw | 1000 | 210 | 12 |
| Oil palm empty fruit bunches | 950 | 190 | 9 |
| Wood chips (cedar) | 250 | 80 | 10 |
| Bagasse (Example 1) | 1150 | 195 | 10 |

Comparative Example 3

For a comparison with Example 4, an examination example will be described in which a stand-still reaction or a stirring reaction was carried out, using rice straw (moisture content: 10%), oil palm empty fruit bunches (moisture content: 15%), and cedar wood chips (moisture content: 5%). The same examination as that carried out in in Comparative Examples 1 and 2 was carried out using the above-described respective raw materials.

In carrying out the stand-still reaction, each of the raw material biomasses obtained in Example 4 and a 0.43% aqueous solution of sodium hydroxide were introduced into a stainless steel container with a capacity of 10 L, according to the amounts shown in Table 9.

In carrying out the stirring reaction, each of the raw material biomasses obtained in Example 4 and a 0.43% aqueous solution of sodium hydroxide were introduced into a reaction vessel with a capacity of 8 L, according to the amounts shown in Table 9.

In the same manner as in Comparative Examples 1 and 2, each of the resulting samples was filtered through a stainless steel strainer with an aperture of 3 mm to obtain a filtrate, and the solid component remaining on the upper surface of the strainer was pressed with a hand against the strainer surface to squeeze out the remaining liquid. The thus obtained liquid component was added to the filtrate to obtain an extraction liquid. The resulting extraction liquid obtained for each raw material biomass under stand-still or stirring condition was analyzed with the method described in Reference Example 1, and the results are shown in Table 10. The pH of each liquid component after the reaction is also shown below.

TABLE 9

| Raw material Biomass | Moisture content | Charged amount | Added amount of alkaline solution | Alkali concentration | Alkaline reaction amount |
|---|---|---|---|---|---|
| Unit | % | kg | kg | % | mg/g |
| Rice straw | 10 | 0.275 | 5.2 | 0.43 | 90.3 |
| Oil palm empty fruit bunches | 15 | 0.29 | 5.2 | 0.43 | 90.7 |
| Wood chips (cedar) | 5 | 0.26 | 5.2 | 0.43 | 90.5 |

TABLE 10

| | Reaction | | | |
|---|---|---|---|---|
| Raw | Stand-still reaction | | Stirring reaction | |
| material | Coumaric acid [mg/L] | Vanillin [mg/L] | Coumaric acid [mg/L] | Vanillin [mg/L] |
| Rice straw | 850 | 9 | 870 | 9 |
| Oil palm empty fruit bunches | 860 | 5 | 880 | 5 |
| Wood chips (cedar) | 210 | 7 | 210 | 7 |

Example 5: Examination of Temperature of Alkaline Filtrate

An examination was carried out, varying the conditions of the reaction temperature in Example 1. Specifically, the reaction temperature was varied such that both the initial temperature of the aqueous solution of sodium hydroxide and the temperature during the reaction of the alkaline filtrate were adjusted to 70° C., 75° C., 80° C., 90° C. or 95° C. The reaction conditions were unified to those described in Example 1 in which the concentration of the aqueous solution of sodium hydroxide was set to 0.5% and the reaction time was set to 2.0 hours, and an extraction liquid and a solid component were obtained by filtration, for each reaction temperature.

Further, the solid component was filtered through a stainless steel strainer with an aperture of 3 mm, in the same manner as in Example 1, and the solid component remaining on the upper surface of the strainer was pressed with a hand against the strainer surface to squeeze out the remaining liquid. The thus obtained liquid component was added to the extraction liquid. The resulting final extraction liquid obtained for each reaction temperature was analyzed with the method described in Reference Example 1, and the results are shown in Table 11.

TABLE 11

| Reaction temperature [° C.] | Coumaric acid [mg/L] | Ferulic acid [mg/L] |
|---|---|---|
| 70° C. | 560 | 80 |
| 75° C. | 590 | 85 |
| 80° C. | 980 | 170 |
| 90° C. (Example 1) | 1150 | 195 |
| 95° C. | 1180 | 200 |

Example 6: Examination Using Potassium Hydroxide

Potassium hydroxide was used instead of sodium hydroxide, as an alkaline substance to be used. The reaction time was set to 2.0 hours, and an extraction liquid and a cellulose-containing solid component were obtained by filtration, according to the method described in Example 1. Further, the solid component was filtered through a stainless steel strainer with an aperture of 3 mm in the same manner as in Example 1, and the solid component remaining on the upper surface of the strainer was pressed with a hand against the strainer surface, to squeeze out the remaining liquid. The thus obtained liquid component was added to the extraction liquid. The resulting final extraction liquid obtained for each set of reaction conditions was analyzed with the method described in Reference Example 1, and the results are shown in Table 12. A comparison of Table 2 (sodium hydroxide) with Table 12 (potassium hydroxide) has revealed that, using potassium hydroxide as an alkaline substance, an amount of from 1.5 to 2 times the amount of sodium hydroxide, on a weight basis, is required.

TABLE 12

| Reaction conditions | | | Evaluation results | | |
|---|---|---|---|---|---|
| Alkali concentration [%] | Alkaline reaction amount [mg/g] | Alkaline reaction time [hr] | Coumaric acid [mg/L] | Ferulic acid [mg/L] | Vanillin [mg/L] |
| 0.4 | 72 | 2.0 | 920 | 175 | 7 |
| 0.6 | 108 | 2.0 | 980 | 180 | 8 |
| 0.8 | 144 | 2.0 | 1050 | 195 | 9 |
| 1.0 | 180 | 2.0 | 1150 | 205 | 12 |
| 1.2 | 216 | 2.0 | 1150 | 210 | 13 |

Example 7: Preparation of Mixed Crystals of Coumaric Acid and Ferulic Acid

An alkaline reaction (alkaline reaction amount: 90 mg/g biomass, Reaction time: 2 hours) was carried out for a plurality of times in accordance with the method described in Example 1, to obtain a total of 100 kg (about 100 L) of an extraction liquid. The resulting extraction liquid was subjected to evaporative concentration, using a plate-type concentrator (Global Concentration Testing Equipment, Model GY-02; manufactured by Hisaka Works, Ltd.) to obtain a concentrate (5 L, 80° C.) and a distillate. Both of the thus obtained liquids were diluted, and the content of each of hydroxycinnamic acids measured according to the method described in Reference Example 1. The results are shown in Table 14. The use of the plate-type concentrator has prevented the components from mixing into the distillate side and from being detected therein.

TABLE 13

| Contents | Coumaric acid [g/L] | Ferulic acid [g/L] | Vanillin [g/L] |
|---|---|---|---|
| Evaporation concentrate | 23 | 3.6 | 0.2 |
| Distillate | Not detected | Not detected | Not detected |

Further, when the above-described concentrate was stored in a refrigerator maintained at 4° C. for one day, the deposition of 100 g of crystals was observed. The purity of the resulting crystals was measured to be 99% or more (the weight of coumaric acid and ferulic acid with respect to the weight of the total solids including components other than coumaric acid and ferulic acid), and it has been confirmed that the resulting crystals are high-purity crystals of coumaric acid and ferulic acid.

When the evaporative concentration was carried out in the same manner as described above, using an evaporator, coumaric acid and ferulic acid were detected in the distillate, in amounts of 100 mg/L or more.

Example 8: Examination of Simulated Facing Contact Extraction

A unit was prepared that includes: a bottom surface provided with punched holes having a size of 3 mm; and an acrylic cylinder that is attached by adhesion onto the bottom surface, which is capable of accommodating biomass therein, and allows for self-weight filtration. The above-described unit was configured such that the filtrate obtained through the punched holes can be reintroduced from above the acrylic cylinder to be subjected to refiltration, in a convection oven capable of maintaining a 90° C. environment. A reaction was carried out, using the above-described system, and using 100 g of bagasse and 900 g of an alkaline solution. The following Method A or Method B was used as the reaction method.

Method A

The above-described unit was operated at 90° C. for one hour in the same manner as in Example 1.

Method B

To simulate the facing contact between bagasse with an alkaline solution, three systems of the above-described units (hereinafter, referred to as Units 1, 2 and 3) were prepared. In Unit 1, the alkaline filtrate obtained from Unit 2 was reacted with ground bagasse for 20 minutes. Next, in Unit 2, the alkaline filtrate obtained from Unit 3 was reacted for 20 minutes, with the cellulose solid component after being treated in Unit 1 for 20 minutes. Next, in Unit 3, the cellulose solid component after being treated in Unit 2 was reacted with a 0.5% aqueous solution of sodium hydroxide for 20 minutes.

The alkaline filtrate obtained by Method A, and the alkaline filtrate obtained after the reaction in Unit 1 in Method B, were each subjected to a concentration analysis according to the method described in Reference Example 1.

The results are shown in Table 14.

It can be seen from Table 14 that the use of Method B resulted in an increase in the amounts of coumaric acid and ferulic acid produced. The results revealed that the facing contact has served to improve the reaction efficiency.

TABLE 14

| Reaction Method | Alkaline filtrate | |
|---|---|---|
| | Coumaric acid [mg/L] | Ferulic acid [mg/L] |
| Method A | 1000 | 180 |
| Method B | 1100 | 190 |

The present patent application is based upon and claims the benefit of priority from previously filed Japanese Patent Application No. 2016-066898 (filed on Mar. 29, 2016), the entire disclosure of which is incorporated herein by reference.

The invention claimed is:

1. A method of producing hydroxycinnamic acids, the method comprising the steps of:
   obtaining an alkaline filtrate by allowing an alkaline aqueous medium to pass through a cellulose-containing biomass; and
   obtaining a hydroxycinnamic acid extraction liquid by allowing the alkaline filtrate to repeatedly pass through the cellulose-containing biomass.

2. The method of producing hydroxycinnamic acids according to claim 1, further comprising the step of separating the hydroxycinnamic acids from the hydroxycinnamic acid extraction liquid, by at least one method selected from an evaporative concentration method and a recrystallization method.

3. The method of producing hydroxycinnamic acids according to claim 2, wherein the evaporative concentration method is carried out using a plate-type concentrator.

4. The method of producing hydroxycinnamic acids according to claim 1, wherein the hydroxycinnamic acids are hydroxycinnamic acid, hydroxybenzoic acid or methoxy group-substituted products of these compounds.

5. The method of producing hydroxycinnamic acids according to claim 1, wherein the hydroxycinnamic acids are at least one of coumaric acid, ferulic acid and vanillin.

6. The method of producing hydroxycinnamic acids according to claim 1, wherein the step of obtaining the alkaline filtrate comprises supplying the cellulose-containing biomass and the alkaline aqueous medium to a filtration apparatus, and allowing the alkaline aqueous medium to pass through the cellulose-containing biomass using the filtration apparatus.

7. The method of producing hydroxycinnamic acids according to claim 1, wherein the alkaline aqueous medium or the alkaline filtrate is allowed to pass through the cellulose-containing biomass by self-weight filtration in the direction of gravity.

8. The method of producing hydroxycinnamic acids according to claim 1, wherein the alkaline aqueous medium and the alkaline filtrate are maintained substantially at the same temperature.

9. The method of producing a hydroxycinnamic acids according to claim 1, wherein at least one of the alkaline aqueous medium and the alkaline filtrate has a temperature of 80° C. or higher and 100° C. or lower.

10. The method of producing hydroxycinnamic acids according to claim 1, wherein the alkaline filtrate comprises acetic acid or a salt thereof.

11. The method of producing hydroxycinnamic acids according to claim 1, wherein the cellulose-containing biomass has been sifted through a sieve with an aperture of 30 mm or more.

12. The method of producing hydroxycinnamic acids according to claim 1, wherein the cellulose-containing biomass has been subjected to a dry grinding treatment.

13. The method of producing hydroxycinnamic acids according to claim 1, wherein the cellulose-containing biomass is an herbaceous biomass.

14. The method of producing hydroxycinnamic acids according to claim 1, wherein the alkaline aqueous medium and the alkaline filtrate comprise at least one hydroxide selected from sodium hydroxide and potassium hydroxide.

15. The method of producing hydroxycinnamic acids according to claim 1, wherein a period of time during which the alkaline filtrate is repeatedly passed through the cellulose-containing biomass is 30 minutes or more and three hours or less.

16. The method of producing hydroxycinnamic acids according to claim 1, wherein the alkaline filtrate has a pH of 10 or more and 12 or less.

\* \* \* \* \*